United States Patent
Jeong et al.

(10) Patent No.: US 8,791,478 B2
(45) Date of Patent: Jul. 29, 2014

(54) ORGANIC LIGHT EMITTING DISPLAY DEVICE

(71) Applicant: LG Display Co., Ltd., Seoul (KR)

(72) Inventors: YunSik Jeong, Busan (KR); Jaewook Kwon, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 13/707,133

(22) Filed: Dec. 6, 2012

(65) Prior Publication Data
US 2014/0117314 A1    May 1, 2014

(30) Foreign Application Priority Data
Nov. 1, 2012    (KR) .................. 10-2012-0122906

(51) Int. Cl.
*H01L 23/522* (2006.01)
*H01L 23/528* (2006.01)
*H01L 23/538* (2006.01)

(52) U.S. Cl.
USPC ............ 257/91; 257/40; 315/169.3; 345/206

(58) Field of Classification Search
None
See application file for complete search history.

(56) References Cited

U.S. PATENT DOCUMENTS

| | | | |
|---|---|---|---|
| 6,531,815 | B1 | 3/2003 | Okuyama et al. |
| 7,851,994 | B2 * | 12/2010 | Park ............................. 313/504 |
| 2002/0044250 | A1 * | 4/2002 | Yoo et al. ...................... 349/149 |
| 2004/0245920 | A1 * | 12/2004 | Nakamura .................... 313/504 |
| 2005/0057461 | A1 | 3/2005 | Suh et al. |
| 2006/0017665 | A1 * | 1/2006 | Ko et al. ......................... 345/76 |
| 2008/0012474 | A1 * | 1/2008 | Sung et al. .................... 313/504 |
| 2008/0036388 | A1 * | 2/2008 | Jung et al. .................. 315/169.3 |
| 2008/0048948 | A1 | 2/2008 | Koh et al. |
| 2009/0184899 | A1 * | 7/2009 | Kim et al. ....................... 345/76 |
| 2011/0157114 | A1 | 6/2011 | Ko et al. |
| 2013/0093654 | A1 | 4/2013 | Park et al. |
| 2014/0014950 | A1 * | 1/2014 | Hara et al. ...................... 257/43 |

FOREIGN PATENT DOCUMENTS

| | | |
|---|---|---|
| JP | 2006-039541 A | 2/2006 |
| JP | 2008-052248 A | 3/2008 |
| JP | 2009-169374 A | 7/2009 |
| KR | 10-2006-0047947 A | 5/2006 |
| WO | WO 2012/090432 A1 | 7/2012 |

OTHER PUBLICATIONS

Office Action for Japanese Patent Application No. JP 2012-279300, mailed Jan. 9, 2014, 8 Pages.
Office Action for Korean Patent Application No. KR 10-2012-0122906, Jun. 16, 2014, 6 Pages (With concise explanation of relevance).

* cited by examiner

*Primary Examiner* — Thomas L Dickey
*Assistant Examiner* — Joseph Schoenholtz
(74) *Attorney, Agent, or Firm* — Fenwick & West LLP

(57) ABSTRACT

Disclosed is an organic light emitting display device. The organic light emitting display device includes a plurality of pixels that include a pixel circuit connected to a gate line, a data line, and a high-level power line, and an emission cell formed between an anode electrode connected to the pixel circuit and a cathode electrode layer receiving low-level power. The organic light emitting display device includes a display panel including a plurality of first pad parts, second pad parts, and cathode connection parts, a plurality of first flexible circuit films respectively connected to the first pad parts to supply the low-level power to a low-level power pad of each of the first pad parts, and a plurality of second flexible circuit films respectively connected to the second pad parts to supply the high-level power to a high-level power pad of each of the second pad parts.

11 Claims, 9 Drawing Sheets

ORGANIC LIGHT EMITTING DISPLAY DEVICE

CROSS-REFERENCE TO RELATED APPLICATIONS

This application claims the benefit of the Korean Patent Application No. 10-2012-0122906 filed on Nov. 1, 2012, which is hereby incorporated by reference as if fully set forth herein.

BACKGROUND

1. Field of the Invention

The present invention relates to an organic light emitting display device, and more particularly, to an organic light emitting display device that minimizes non-uniform luminance due to the drop of a voltage caused by a line resistance, and facilitates the supply of high-level power and low-level power.

2. Discussion of the Related Art

With the advance of multimedia, the importance of flat panel display (FPD) devices is increasing recently. Therefore, various FPD devices such as liquid crystal display (LCD) devices, plasma display panel (PDP) devices, and organic light emitting display devices are being used practically. In such FPD devices, the organic light emitting display devices having a self-emission type have a fast response time, low power consumption, high resolution, and an large screen, and thus are attracting much attention as next-generation FPD devices.

Generally, as illustrated in FIG. 1, a related art organic light emitting display device includes a display panel 10, a plurality of gate drivers 20, a plurality of data drivers 30, a plurality of flexible circuit films 40 for supplying power, and a printed circuit board (PCB) 50.

The display panel 10 includes a first substrate 12 including a plurality of pixels P and a cathode electrode layer CE, and a second substrate 14 facing-coupled to the first substrate 12.

The plurality of pixels P are respectively formed in a plurality of pixel areas defined by intersections between a plurality of gate lines and a plurality of data lines DL that are formed on the first substrate 12 to intersect. Each of the pixels P includes a pixel circuit PC and an emission cell EL.

The pixel circuit PC is connected to a gate line GL, a data line DL, and a high-level power line PL. The pixel circuit PC supplies a data current, corresponding to a data signal supplied to the data line DL, to an emission cell EL in response to a gate signal supplied to the gate line GL. For example, the pixel circuit PC includes a switching thin film transistor T1, a driving thin film transistor T2, and a capacitor C.

The switching thin film transistor T1 is switched on according to the gate signal supplied to the gate line GL, and supplies a data voltage, supplied from the data line DL, to the driving thin film transistor T2. The driving thin film transistor T is switched on with the data voltage supplied from the switching thin film transistor T1, generates a data current corresponding to the data voltage, and supplies the data current to the emission cell EL. The capacitor C holds the data voltage supplied to the driving thin film transistor T2, during one frame.

The emission cell EL includes an anode electrode (not shown) connected to the pixel circuit PC, and an organic layer (not shown) formed on the anode electrode and the cathode electrode layer CE. Here, the organic layer may be formed to have a structure of a hole transport layer/organic emission layer/electron transport layer or a structure of a hole injection layer/hole transport layer/organic emission layer/electron transport layer/electron injection layer. Furthermore, the organic layer may further include a function layer for enhancing the emission efficiency and/or service life of the organic emission layer.

The cathode electrode layer CE is formed to cover an entire area except an edge of the first substrate 12, and connected to the emission cell EL of each pixel P. The cathode electrode layer CE receives low-level power from the flexible circuit film 50 for supplying power.

A plurality of data pad parts (not shown), a plurality of gate pad parts (not shown), and a plurality of power supply pad parts (not shown) are prepared in an inactive area of the first substrate 12.

Each of the data pad parts includes a plurality of data pads respectively connected to the data lines DL.

Each of the gate pad parts includes a plurality of gate pads respectively connected to the gate lines DL.

Each of the power supply pad parts includes a plurality of high-level power pads respectively connected to the high-level power lines PL, and a plurality of low-level power pads connected to the cathode electrode layer CE. Each of the power supply pad parts is disposed between adjacent data pad parts.

The second substrate 14 is formed of glass or metal in a plate shape, and facing-coupled to the first substrate 12, thereby protecting the emission cell EL of each pixel P (formed in the first substrate 12) from moisture, oxygen, etc. In this case, the second substrate 14 is adhered to an inactive area of the first substrate 12 by a sealing member (not shown) that is formed to surround an active area of the first substrate 12 including the plurality of pixels P.

Each of the gate drivers 20 is connected to a corresponding gate pad part among the gate pad parts formed in a left or right inactive area of the first substrate 12, and supplies the gate signal to a corresponding gate line GL through the gate pad of the corresponding gate pad part. To this end, each of the gate drivers 20 includes a gate flexible circuit film 22 adhered to a corresponding gate pad part, and a gate driving integrated circuit (IC) 24 that is mounted on the gate flexible circuit film 22, generates the gate signal, and supplies the gate signal to a corresponding gate line GL through the gate flexible circuit film 22 and a corresponding gate pad.

Each of the data drivers 30 is connected to a corresponding data pad part among the data pad parts formed in an upper inactive area of the first substrate 12, and supplies a data signal to a corresponding data line DL through the data pad of the corresponding data pad part. To this end, each of the data drivers 30 includes a data flexible circuit film 32 adhered to a corresponding data pad part, and a data driving IC 34 that is mounted on the data flexible circuit film 32, generates the data signal, and supplies the data signal to a corresponding data line DL through the data flexible circuit film 32 and a corresponding data pad.

Each of the flexible circuit films 40 for supplying power is connected to a corresponding power supply pad part among the power supply pad parts formed in the upper inactive area of the first substrate 12, and disposed between adjacent data pad parts. Each of the flexible circuit films 40 supplies high-level power to a corresponding high-level power line PL through a high-level power pad of a corresponding power supply pad part, and supplies low-level power to the cathode electrode layer CE through a low-level power pad of the corresponding power supply pad part.

The PCB 50 is connected to the data driver 30 and the flexible circuit films 40 for supplying power, supplies digital input data to the data driver 30, and supplies the high-level power and the low-level power to the flexible circuit films 40.

In the related art organic light emitting display device, since the high-level power and the low-level power are supplied through the power supply pad parts prepared at an upper side of the display panel 10, a voltage decreases progressively closer from an upper side to a lower side of the display panel 10 due to the drop of a voltage (IR drop) caused by a line resistance, causing non-uniform luminance.

Furthermore, as the related art organic light emitting display device becomes higher in resolution, when the display panel 10 has super high resolution, the number of data lines DL, the number of gate lines GL, and the number of high-level power lines PL increase by two times. Due to this reason, the power supply pad part cannot be disposed in a space between adjacent data drivers 30, and thus, it is impossible to supply the high-level power and the low-level power through the flexible circuit film 40.

The above-described background is possessed by the inventor of the application for deriving the invention, or is technology information that has been acquired in deriving the invention. The above-described background is not necessarily known technology disclosed to the general public before the application of the invention.

SUMMARY

Accordingly, the present invention is directed to an organic light emitting display device that substantially obviates one or more problems due to limitations and disadvantages of the related art.

An aspect of the present invention is directed to an organic light emitting display device that minimizes non-uniform luminance due to the drop of a voltage caused by a line resistance, and facilitates the supply of high-level power and low-level power.

Additional advantages and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, there is provided an organic light emitting display device. The organic light emitting display device comprises a display panel that includes plurality of pixels; a cathode layer coupled to the plurality of pixels to supply a first supply voltage to the pixels; a plurality of supply voltage pads; and a plurality of cathode connection parts coupled to the cathode layer to supply the first supply voltage to the cathode layer from the plurality of supply voltage connection pads, wherein each of the cathode connection parts is in contact with the cathode layer through a contact area, wherein the contact area is between 10% and 90% of an overlapping area of the cathode connection part and the cathode layer.

In one embodiment, each cathode connection part comprises an electrode layer that overlaps with the cathode layer, wherein the overlapping area of the cathode connection part and the cathode layer is the overlapping area between the electrode layer and the cathode layer.

In one embodiment, the display panel further comprises gate lines connected to the pixels, and the electrode layer and the gate lines are formed in a same conductive layer.

In one embodiment, each cathode connection part comprises one or more voltage lines connecting the electrode layer with respective ones of the supply voltage connection pads.

In one embodiment, for each cathode connection part, the contact area comprises one or more intermediate conductive layers located between the cathode layer and the electrode layer that connect the cathode layer with the electrode layer.

In one embodiment, the display panel further comprises data lines connected to the pixels, and at least one of the intermediate conductive layers and the data lines are formed in a same conductive layer.

In one embodiment, a first layer of the intermediate conductive layers is formed from Copper and a second metal layer of the intermediate conductive layers is formed from Molybdenum-Titanium.

In one embodiment, at least one of the intermediate conductive layers and supply voltage connection pads are formed from a same conductive material that is transparent.

In one embodiment, the one or more intermediate conductive layers comprise a first intermediate conductive layer in contact with the electrode layer; a second intermediate conductive layer on the first intermediate conductive layer and in contact with the first intermediate conductive layer through a hole in a planarizing layer; and wherein the cathode layer is in contact with the second intermediate conductive layer through a hole in a bank layer.

In one embodiment, the display panel further comprises gate lines and data lines connected to the pixels, and wherein: the electrode layer and the gate lines are formed in a first conductive layer during a first process step; the first intermediate contact layer and data lines are formed in a second conductive layer during a second process step, and the second intermediate contact layer and the supply voltage pads are formed from a same conductive material that is transparent.

In one embodiment, the overlapping area is polygonal, for example, in a triangular shape. In one embodiment, the contact area is rectangular.

In one embodiment, there is provided an organic light emitting display device comprising a display panel including a plurality of pixels that include a pixel circuit connected to a gate line, a data line, and a high-level power line, and an emission cell formed between an anode electrode connected to the pixel circuit and a cathode electrode layer receiving low-level power, which includes: a display panel including a plurality of first pad parts that include a data pad connected to the data line, and a low-level power pad receiving the low-level power, a plurality of second pad parts that include a gate pad connected to the gate line, and a high-level power pad connected to the high-level power line parallel to the gate line, and a plurality of cathode connection parts that electrically connect the low-level power pad to the cathode electrode layer; a plurality of first flexible circuit films respectively connected to the first pad parts, and supplying the low-level power to the low-level power pad; and a plurality of second flexible circuit films respectively connected to the second pad parts, and supplying the high-level power to the high-level power pad.

Each of the cathode connection parts may be formed at both sides of a corresponding first pad part to overlap the cathode electrode layer, and may supply the low-level power, supplied from the low-level power pad, to the cathode electrode layer.

Each of the cathode connection parts formed in respective spaces between the plurality of first pad parts may be connected to a low-level power pad of two adjacent first pad parts.

Each of the cathode connection parts may include: a low-level electrode layer electrically connected to the cathode electrode layer; and a low-level power link line connecting the low-level electrode layer to the low-level power pad.

Each of the cathode connection parts may further include: an additional electrode layer electrically connected to the low-level electrode layer; and a low-level electrode pad electrically connected to the additional electrode layer, and electrically connected to the cathode electrode layer through a contact hole.

The organic light emitting display device may further include: a first PCB supplying the low-level power to the first flexible circuit films; and a second PCB supplying the high-level power to the second flexible circuit films.

Each of the second pad parts may further include an additional low-level power pad receiving the low-level power, and the display panel may further include an additional cathode connection part electrically connecting the additional low-level power pad to the cathode electrode layer.

The additional cathode connection part may be formed at both sides of each of the second pad parts to overlap the cathode electrode layer, and may supply the low-level power, supplied from the additional low-level power pad, to the cathode electrode layer.

Each of the second flexible circuit films may additionally supply the low-level power to the additional low-level power pad.

The organic light emitting display device may further include: a first PCB supplying the low-level power to the first flexible circuit films; and a second PCB supplying the high-level power and the low-level power to the second flexible circuit films.

Some of the first pad parts may further include a high-level power transfer pad receiving the high-level power, and the display panel may further include: a plurality of high-level power transfer lines that supply the high-level power, supplied to the high-level power transfer pad, to a first-position second pad part and last-position second pad part of the plurality of second pad parts; and a plurality of high-level power connection lines that are formed in respective spaces between the second pad parts other than the first-position second pad part and last-position second pad part, and supply the high-level power, supplied to a high-level power pad of a previous-stage second pad part, to a high-level power pad of a next-stage second pad part.

The organic light emitting display device may further include a PCB supplying the low-level power to the first flexible circuit films, and supplying both the low-level power and the high-level power to some of the first flexible circuit films, wherein the some first flexible circuit films of first flexible circuit films supply the high-level power, supplied from the PCB, to the high-level power transfer pad.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Figure 1:
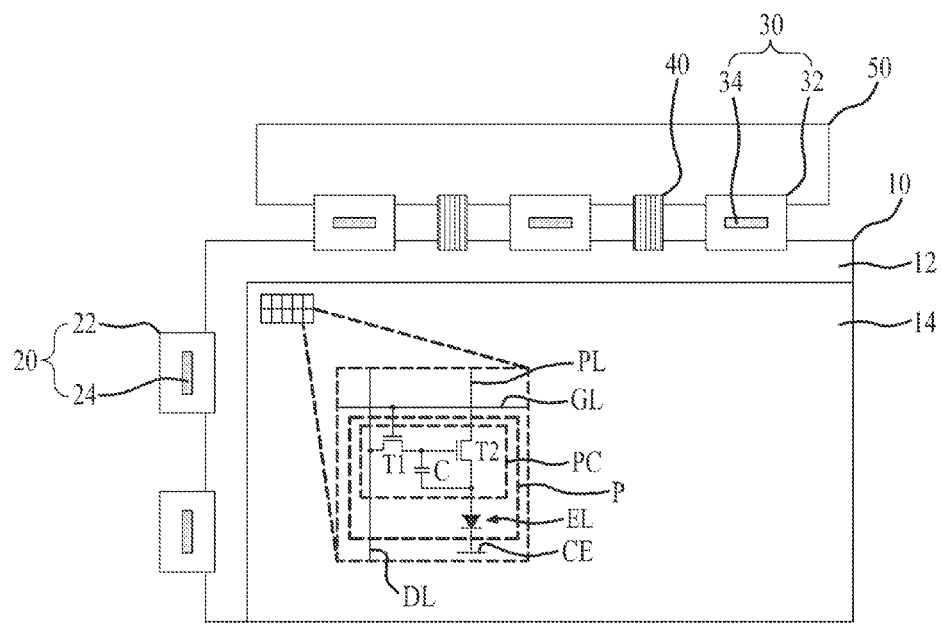
FIG. 1 is a view schematically illustrating a related art organic light emitting display device.

Reference will now be made in detail to the exemplary embodiments of the present invention, examples of which are illustrated in the accompanying drawings. Wherever possible, the same reference numbers will be used throughout the drawings to refer to the same or like parts.

In the specification, although illustrated in the drawing, it is noted that like reference numerals denote like elements in appreciating the drawings.

The terms described in the specification should be understood as follows.

As used herein, the singular forms "a", "an" and "the" are intended to include the plural forms as well, unless the context clearly indicates otherwise. The terms first and second are for differentiating one element from the other element, and these elements should not be limited by these terms.

It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The term "at least one" should be understood as including any and all combinations of one or more of the associated listed items. For example, the meaning of "at least one of a first item, a second item, and a third item" denotes the combination of all items proposed from two or more of the first item, the second item, and the third item as well as the first item, the second item, or the third item.

Hereinafter, embodiments of the present invention will be described in detail with reference to the accompanying drawings.

Figure 2:
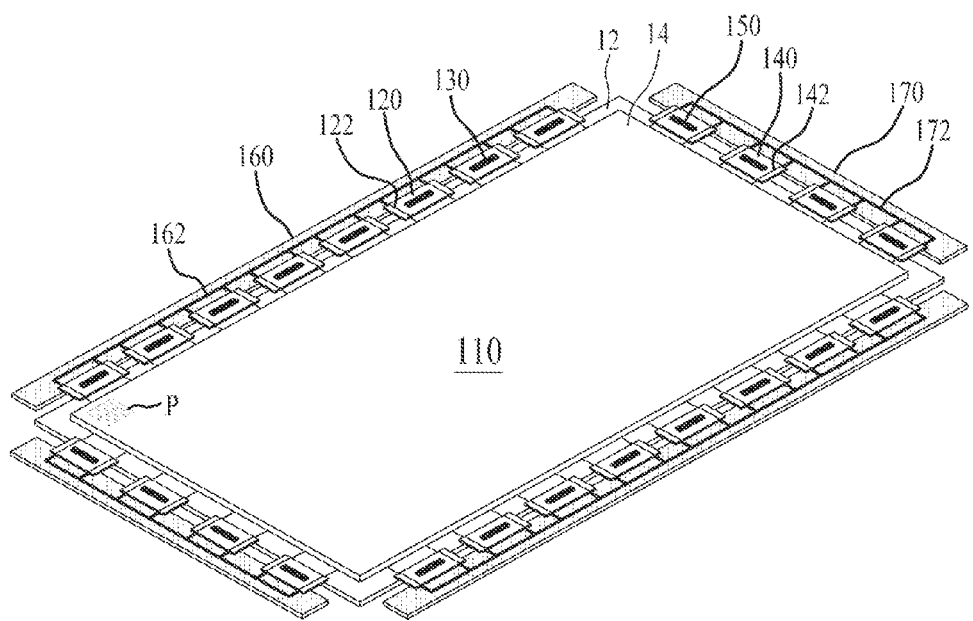
FIG. 2 is a perspective view schematically illustrating an organic light emitting display device according to a first embodiment of the present invention.
Figure 3:
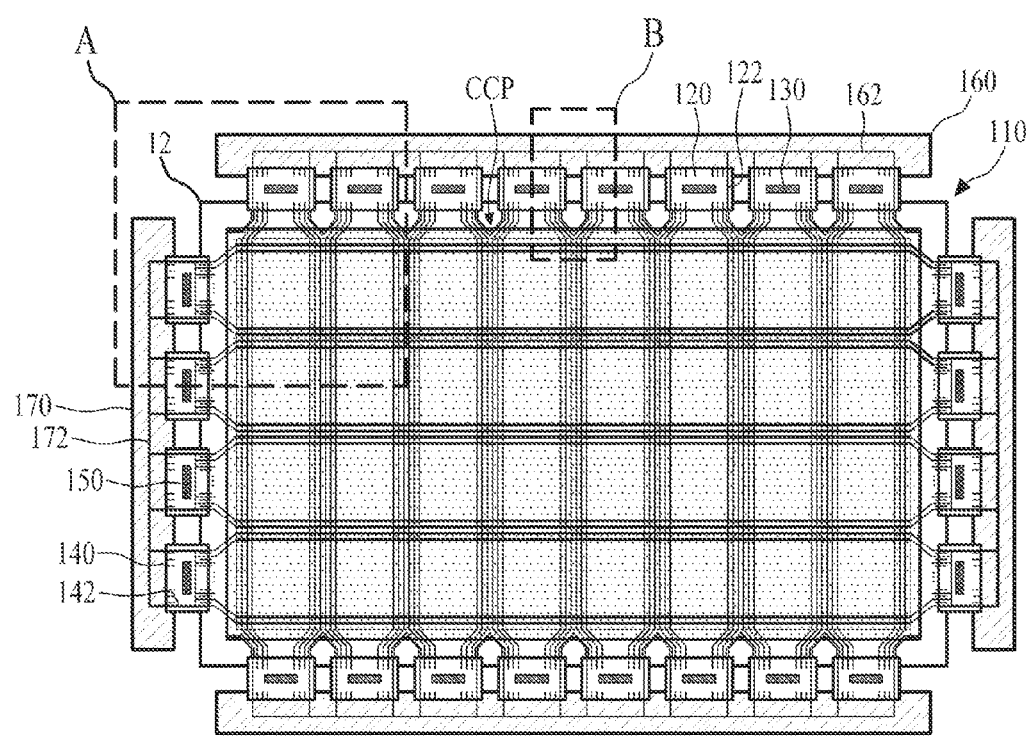
FIG. 3 is a plan view for describing a plurality of first flexible circuit films and second flexible circuit films (which are connected to a first substrate) of FIG. 2.
Figure 4:
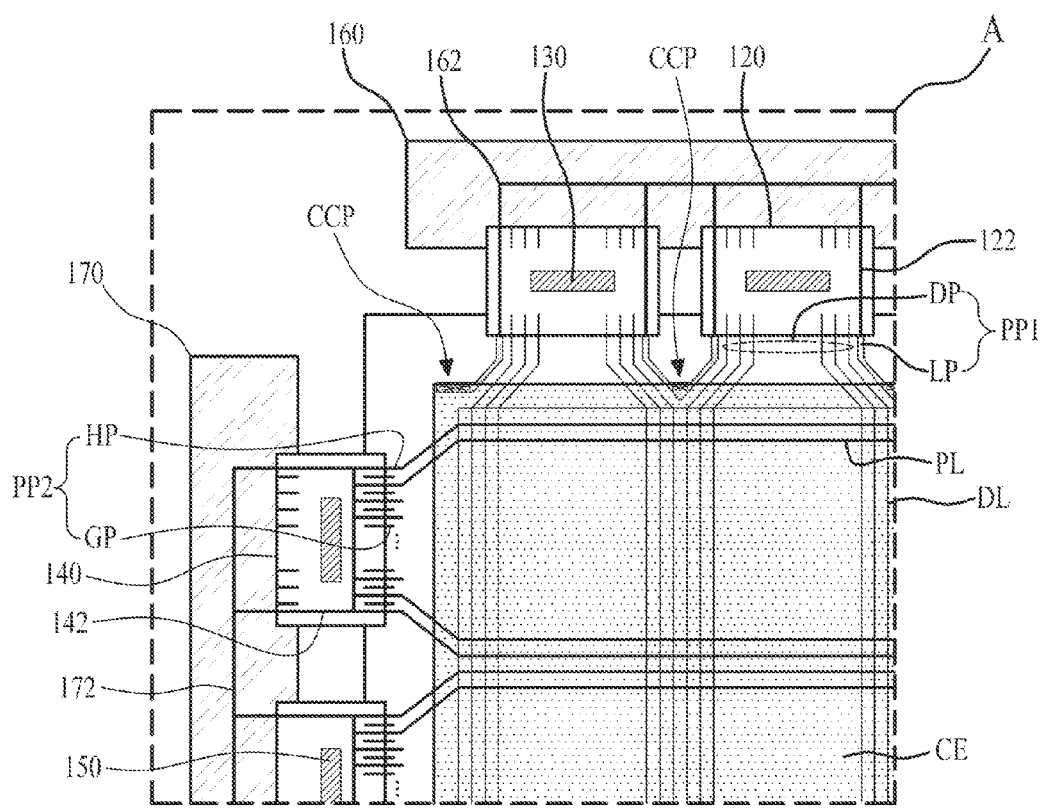
FIG. 4 is an enlarged view of a portion A of FIG. 3.

FIG. 2 is a perspective view schematically illustrating an organic light emitting display device according to a first embodiment of the present invention. FIG. 3 is a plan view for describing a plurality of first flexible circuit films and second flexible circuit films (which are connected to a first substrate) of FIG. 2. FIG. 4 is an enlarged view of a portion A of FIG. 3.

Referring to FIGS. 2 and 3, the organic light emitting display device according to the first embodiment of the present invention includes a display panel 110, a plurality of first flexible circuit films 120, a plurality of data driving ICs 130, a plurality of second flexible circuit films 140, and a plurality of gate driving ICs 150.

The display panel 110 includes first and second substrates 12 and 14 that are facing-coupled to each other.

Referring to FIGS. 2-4, the first substrate 12 includes a plurality of data lines DL, a plurality of gate lines (not shown), a plurality of high-level power lines PL, a plurality of pixels P, a cathode electrode layer CE, a plurality of first pad parts PP1, a plurality of second pad parts PP2, and a plurality of cathode connection parts CCP.

The data lines DL are parallel to each other and formed at certain intervals in a first direction of the first substrate 12. Here, the first direction may be a direction parallel to a short side of the first substrate 12.

The gate lines are parallel to each other and formed at certain intervals in a second direction intersecting with and being perpendicular to the first direction.

The high-level power lines PL are formed at certain intervals in the second direction, and each of high-level power lines PL is disposed between adjacent gate lines. In this case, one gate line or a predetermined number of gate lines may be formed between two adjacent high-level power lines PL. The high-level power lines PL carry a high-level power supply voltage (e.g. VDD).

The plurality of pixels P are respectively formed in a plurality of pixel areas defined by intersections between the data lines DL and the gate lines. Each of the pixels P is connected to a data line DL, a gate line, and a high-level power line PL that are adjacent thereto. In response to a gate signal supplied to a corresponding gate line, each pixel P emits light with a current (which flows from a corresponding high-level power line PL to the cathode electrode layer CE) in correspondence with a data voltage supplied to a corresponding data line DL, thereby displaying a certain image. To this end, each pixel P includes a pixel circuit (not shown) and an emission cell (not shown). The pixels P of the present invention having the above-described configuration, as illustrated in FIG. 1, are the same as the pixels of the related art, and thus, the description of the related art is applied to the pixels P of the present invention.

In order to prevent a threshold voltage deviation of a driving thin film transistor, the pixel circuit of each pixel P according to the present invention may further include a compensation circuit (not shown) for compensating for the threshold voltage of the driving thin film transistor.

The compensation circuit includes at least one compensation transistor (not shown) and at least one compensation capacitor (not shown) that are formed inside the pixel circuit. The compensation circuit stores both a data voltage and the threshold voltage of the driving thin film transistor in the capacitor during a detection period for which the threshold voltage of the driving thin film transistor is detected, thereby compensating for the threshold voltage of the driving thin film transistor.

The cathode electrode layer CE, as in a dot-hatched area of FIGS. 3 and 4, is formed to cover an entire area of the first substrate 12 except for an edge of the first substrate 12. The cathode electrode layer CE is also connected to the emission cell of each pixel P. The cathode electrode layer CE receives a low-level power (egg, a low-level supply voltage such as VSS) from the first flexible circuit film 120 and supplies the low-level power to the pixels P.

The first pad parts PP1 are formed at certain intervals in the display panel 110, namely, first and second inactive areas of the first substrate 12 which are parallel. For example, the first inactive area is an upper edge area of the first substrate 12, and the second inactive area is a lower edge area of the first substrate 12. Each of the first pad parts PP1 includes a plurality of data pads DP respectively connected to the data lines DL, and a plurality of low-level power pads LP (also referred to as supply voltage pads) respectively connected to the data lines DL.

The data pads DP are formed at certain intervals, and each of the data pads DP is connected to a corresponding data line DL through a corresponding data link line among a plurality of data link lines (not shown).

The low-level power pads LP are formed at both sides of the first pad part PP1 with a plurality of data pads DP therebetween. In this case, a pair of low-level power pads LP are formed in each of the first pad parts PP1.

The second pad parts PP2 are prepared at certain intervals in the display panel 110, namely, third and fourth inactive areas of the first substrate 12 which are parallel to each other. For example, the second inactive area is a left edge area of the first substrate 12, and the fourth inactive area is a right edge area of the first substrate 12. Each of the second pad parts PP2 includes a plurality of gate pads GP respectively connected to the gate lines, and a plurality of high-level power pads HP respectively connected to the gate lines GL.

The gate pads GP are formed at certain intervals, and each of the gate pads GP is connected to a corresponding gate line through a corresponding gate link line among a plurality of gate link lines (not shown).

Each of the high-level power pads HP is formed between adjacent gate pads GP, and electrically connected to a corresponding high-level power line PL through a corresponding high-level power link line. Here, each of the high-level power lines PL is formed between adjacent gate lines to be parallel to the gate lines. Therefore, each of the high-level power pads HP supplies high-level power, supplied from a corresponding second flexible circuit film 140, to a corresponding high-level power line PL.

The cathode connection parts CCP are formed in the first and second inactive areas of the first substrate 12, and electrically connected to the respective low-level power pads LP. The cathode connection parts CCP are electrically connected to upper and lower edge portions of the cathode electrode layer CE at certain intervals. Therefore, each of the cathode connection parts CCP supplies low-level power, supplied from the low-level power pad LP of the first pad part PP1, to the upper and lower edge portions of the cathode electrode layer CE at certain intervals. In this case, a contact area between the cathode connection part CCP and the cathode electrode layer CE may be set to 10% to 90% of an overlap area between the cathode connection part CCP and the cathode electrode layer CE. That is, when the contact area between the cathode connection part CCP and the cathode electrode layer CE is less than 10% of the overlap area between the cathode connection part CCP and the cathode electrode layer CE, due to the narrow contact area between the cathode connection part CCP and the cathode electrode layer CE, a resistance of the contact area increases, and thus, the heat generation of the cathode connection part CCP increases, causing the burning of the cathode connection part CCP and cathode electrode layer CE. Furthermore, when the contact area between the cathode connection part CCP and the cathode electrode layer CE exceeds 90% of the overlap area between the cathode connection part CCP and the cathode electrode layer CE, it is not easy to connect the cathode connection part CCP and the cathode electrode layer CE.

The leftmost cathode connection parts CCP of the cathode connection parts CCP are connected to a left upper corner portion and left lower corner of the cathode electrode layer CE. Also, the rightmost cathode connection parts CCP of the cathode connection parts CCP is connected to a right upper corner portion and right lower corner of the cathode electrode layer CE. The remaining cathode connection parts CCP are connected to the upper and lower edge portions of the cathode electrode layer CE, at locations corresponding to respective spaces between adjacent first pad parts PP1, at certain intervals.

The second substrate 14 is formed of glass or metal in a plate shape, and facing-coupled to the first substrate 12, thereby protecting the emission cell EL of each pixel P (formed in the first substrate 12) from moisture, oxygen, etc. In this case, the second substrate 14 is adhered to an inactive area of the first substrate 12 by a sealing member (not shown) that is formed to surround an active area of the first substrate 12 including the plurality of pixels P.

Each of the first flexible circuit films 120 is adhered to a corresponding first pad part PP1, and supplies the low-level power to the low-level power pad LP of the first pad part PP1. In this case, a pair of low-level power supply lines 122 electrically connected to the low-level power pad LP are formed in each of the first flexible circuit films 120. Therefore, the low-level power is supplied to the cathode electrode layer CE through the first flexible circuit film 120, the low-level power pad LP, and the cathode connection part CCP.

Each of the first flexible circuit films 120 is formed as a tape carrier package (TCP) or a chip on film (chip on flexible board, COF), and adhered to the first pad part PP1, formed in each of the first and second inactive areas of the display panel 110, by a tape automated bonding (TAB) process. Therefore, the first flexible circuit films 120 may be divided into a plurality of upper first flexible circuit films adhered to the respective pad parts PP1 in the first inactive area, and a plurality of lower first flexible circuit films adhered to the respective pad parts PP1 in the second inactive area.

The data driving ICs 130 are respectively mounted on the first flexible circuit films 120. Each of the data driving ICs 130 generates analog data signals with a data control signal, a plurality of reference gamma voltages, and digital input data inputted through a corresponding first flexible circuit film 120, and supplies the data signals to corresponding data lines DL through the corresponding first flexible film 120 and the data pads DP of the first pad part PP1. In this case, a plurality of data signal supply lines (not shown) that are formed between the pair of low-level power supply lines 122 and electrically connected to the respective data pads DP are formed in each of the first flexible circuit films 120, and moreover, a plurality of signal input lines (not shown) that transfer external digital input data, the data control signal, and the reference gamma voltages to the data driving IC 130 are formed in each of the first flexible circuit films 120.

Each of the second flexible circuit films 140 is adhered to a corresponding second pad part PP2, and supplies the high-level power to the high-level power pad HP of the second pad part PP2. In this case, a pair of high-level power supply lines 142 electrically connected to the high-level power pad HP are formed in each of the second flexible circuit films 140. Therefore, the high-level power is supplied to both sides of the high-level power line PL through the second flexible circuit film 140, the high-level power pad HP, and the high-level power link line.

Each of the second flexible circuit films 140 is formed as a TCP or a COF, and adhered to the second pad part PP2, formed in each of the third and fourth inactive areas of the display panel 110, by the TAB process. Therefore, the second flexible circuit films 140 may be divided into a plurality of upper second flexible circuit films adhered to the respective pad parts PP2 in the third inactive area, and a plurality of lower second flexible circuit films adhered to the respective pad parts PP2 in the fourth inactive area.

The gate driving ICs 150 are respectively mounted on the second flexible circuit films 140. Each of the gate driving ICs 150 generates gate signals according to a gate control signal inputted through a corresponding second flexible circuit film 140, and sequentially supplies the gate signals to corresponding gate lines GL through the corresponding second flexible film 140 and the gate pads GP of the second pad part PP2. A plurality of gate signal supply lines (not shown) that are formed between the pair of high-level power supply lines 142 and electrically connected to the respective gate pads GP are formed in each of the second flexible circuit films 140, and moreover, a plurality of signal input lines (not shown) that transfer an external gate control signal to the gate driving IC 150 are formed in each of the second flexible circuit films 140.

The organic light emitting display device according to the first embodiment of the present invention further includes first and second PCBs 160 and 170.

The first PCB 160 is electrically connected to each of the first flexible circuit films 120 adhered to the respective first pad parts PP1 in the first and second inactive areas of the display panel 110, and supplies the low-level power to the first flexible circuit films 120. To this end, a low-level power input line 162 connected to the low-level power supply line 122 formed in the first flexible circuit film 120 is formed in the first PCB 160.

The first PCB 160 supplies the external digital input data, the data control signal, and the reference gamma voltages to each of the data driving ICs 130.

The second PCB 170 is electrically connected to each of the second flexible circuit films 140 adhered to the respective second pad parts PP2 in the third and fourth inactive areas of the display panel 110, and supplies the high-level power to the second flexible circuit films 140. To this end, a high-level power input line 172 connected to the low-level power supply line 142 formed in the second flexible circuit film 140 is formed in the first PCB 170.

Figure 5:
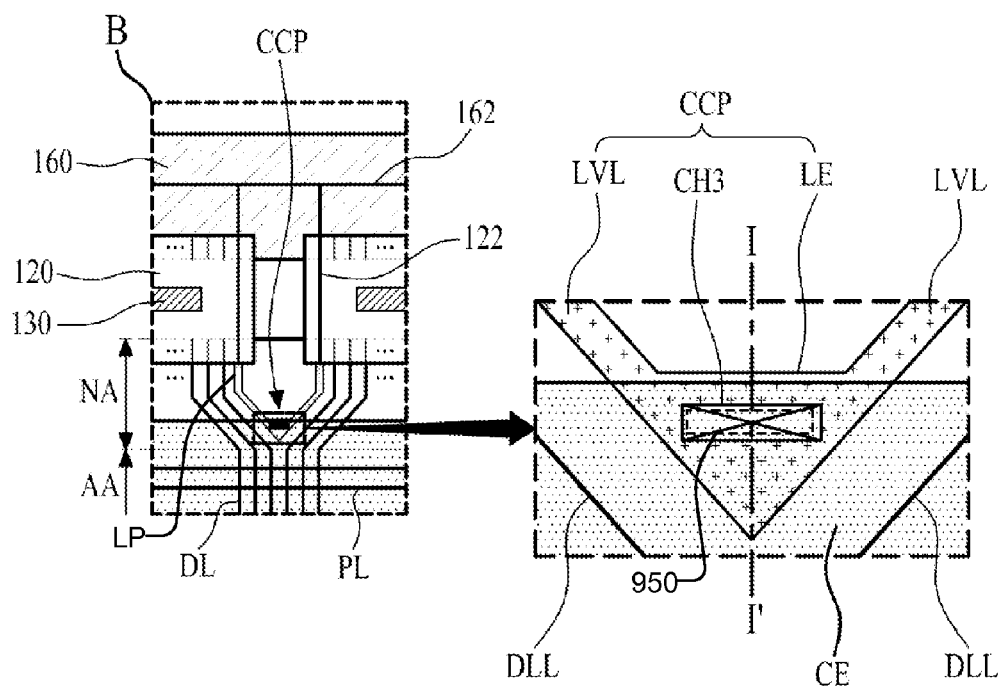
FIG. 5 is an enlarged view of a portion B of FIG. 3.
Figure 6:
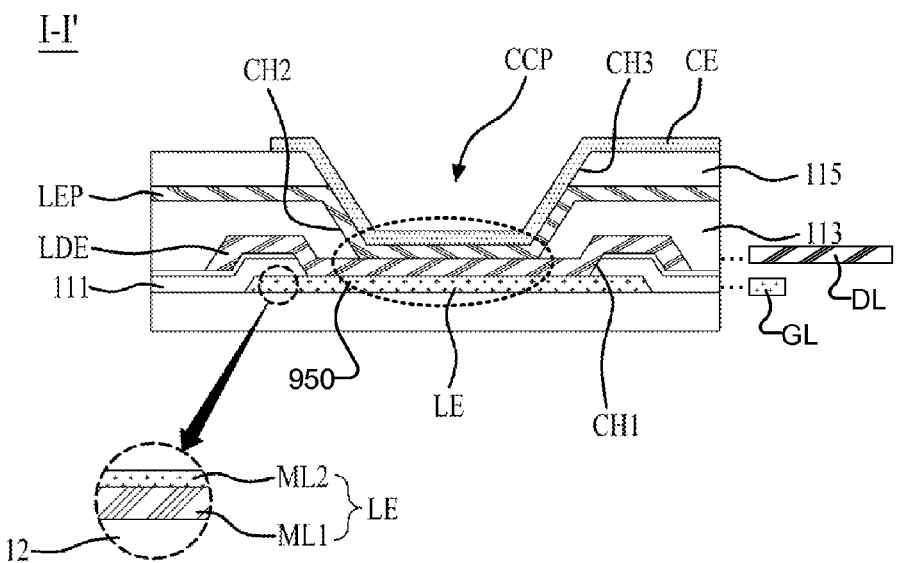
FIG. 6 is a sectional view taken along line I-I' of FIG. 5.

FIG. 5 is an enlarged view of a portion B of FIG. 3. FIG. 6 is a sectional view taken along line I-I' of FIG. 5. FIGS. 5 and 6 are views for describing in detail the structure of the cathode connection part of FIGS. 3 and 4.

Referring to FIGS. 4 to 6, the cathode connection part CCP includes a low-level power link line LVL and a low-level electrode layer LE.

The low-level power link line LVL (i.e. supply voltages link line) is formed in the inactive area NA of the first substrate 12, and connected to the low-level power pad LP of the first pad part PP1. The low-level power link line LVL is separated from a data link line DLL adjacent thereto by a certain distance, and formed in parallel thereto.

A low-level electrode layer LE is formed in the inactive area NA of the first substrate 12 to overlap an edge portion of the cathode electrode layer CE corresponding to a intermediate portion of the cathode electrode layer CE between two adjacent first pad parts PP1. In this case, the low-level electrode layer LE is larger and/or wider than the low-level power link line LVL (which overlaps the edge portion of the cathode electrode layer CE) to have a certain area. The low-level electrode layer LE may be formed in a line shape. However, in consideration of a formation area and resistivity, the low-level power electrode LE is formed here to have a flat plane having a polygonal shape such as a triangular shape. That is, as a contact area 950 between the low-level electrode layer LE and the cathode electrode layer CE increases, burning can be prevented in the cathode connection part CCP and the cathode electrode layer CE. Therefore, the low-level electrode layer LE is formed in a broad inactive area NA between the plurality of first pad parts PP1 including the data pad DP, and thus may be formed to have a broad area such that the contact area 950 between the low-level electrode layer LE and the cathode electrode layer CE increases maximally.

The low-level electrode layer LE of the leftmost cathode connection part CCP of the cathode connection parts CCP is connected to the low-level power pad LP of a first-position first pad part PP1 through one low-level power link line LVL. Also, the low-level electrode layer LE of the rightmost cathode connection part CCP of the cathode connection parts CCP is connected to the low-level power pad LP of a rightmost first pad part PP1 through one low-level power link line LVL. Furthermore, the low-level electrode layer LE of the remaining cathode connection parts CCP is in common connected to the low-level power pads LP of two adjacent first pad parts PP1 through a pair of low-level power link lines LVL.

The low-level power link line LVL and the low-level electrode layer LE are simultaneously formed in a process step that also forms the gate lines GL on the first substrate 12, and may be formed of the same material as that of the gate line GL. Therefore, the low-level power link line LVL and the low-level electrode layer LE may be formed of a material having low resistivity, for decreasing the rising of the low-level power. To this end, the gate line, the low-level power link line LVL, and the low-level electrode layer LE may be formed in a metal layer having at least two layers. As an example, the gate line, the low-level power link line LVL, and the low-level electrode layer LE may be formed in a first metal layer ML1 of Copper (Cu) (which is formed on the first substrate 12) and a second metal layer ML2 of Molybdenum-Titanium (MoTi) that is formed on the first metal layer ML1. As another example, although not shown, the gate line, the low-level power link line LVL, and the low-level electrode layer LE may be formed in a first metal layer ML1 of MoTi (which is formed on the first substrate 12), a second metal layer ML2 of Cu (which is formed on the first metal layer ML1), and a third metal layer ML3 of MoTi that is formed on the second metal layer ML2. Here, the metal layer of Cu may be formed thicker than the metal layer of MoTi.

The low-level electrode LE may be electrically connected to the edge portion of the cathode electrode layer CE through a first contact hole CH1 that is formed in an insulating layer 111 covering the low-level electrode layer LE.

In order to more stably connect the low-level electrode LE and the cathode electrode CE, the cathode connection part CCP further includes several intermediate layers stacked between the lower electrode LE and the cathode electrode CE, such as an additional electrode layer LDE and a low-level electrode pad LEP. The intermediate electrode layers are conductive and serve to electrically connect the cathode layer with the electrode layer.

An additional electrode layer LDE is formed in an island shape on the insulating layer 111 to overlap the low-level electrode layer LE, and electrically connected to the low-level electrode layer LE through the first contact hole CH1 formed on the insulating layer 111. The additional electrode layer LDE is formed simultaneously in a process step that forms the data lines DL, and may be formed of the same material as that of the data line DL. Here, the additional electrode layer LDE and the data line DL may be formed of the same material and in the same structure as the gate line, the low-level power link line LVL, and the low-level electrode layer LE. For example, the additional electrode layer LDE and the data line DL may be formed in a first metal layer (not shown) of Cu and in a second metal layer of MoTi formed on the first metal layer.

The low-level electrode pad LEP is formed in an island shape on a planarizing layer 113 (which covers the additional electrode layer LDE) to overlap the additional electrode layer LDE, and electrically connected to the additional electrode layer LDE through a second contact hole CH2 formed on the planarizing layer 113. Here, the low-level electrode pad LEP is formed simultaneously in a process step that forms the pads of the first and second pad parts PP1 and PP2, and may be formed of a transparent conductive material.

The cathode electrode layer CE is electrically connected to the low-level electrode pad LEP through a third contact hole CH3 that is formed on a bank layer 115 covering the low-level electrode pad LEP. In this case, the bank layer 115 is formed on the low-level electrode pad LEP and the planarizing layer 113 in order for the pixels P to be separately separated from each other. The cathode electrode layer CE is electrically connected to the low-level electrode layer LE through the low-level electrode pad LEP and the additional electrode layer LDE that are formed on the first contact hole CH1. Therefore, the cathode electrode layer CE is electrically connected to the low-level power pad LP through the low-level electrode pad LEP, the additional electrode layer LDE, the low-level electrode layer LE, and the low-level power link line LVL, and receives the low-level power from the first flexible circuit film 120.

In one embodiment, the overlapping area of the cathode connection part CCP and the cathode electrode layer CE can be measured by the overlap between the low-level electrode layer LE and the cathode electrode layer CE. In FIG. 5, the overlapping area is close to the entire size of the lower electrode layer LE. In one embodiment, the contact area 950 between the cathode connection part CCP and the cathode electrode layer CE can be measured by the area of the lower electrode LE that contacts the intermediate layers. For example, in FIG. 6, the size of the contact area 950 is a size of an area in which the cathode electrode layer CE, the low-level electrode pad, additional electrode layer LDE, and the low-level electrode layer LE contact each other. Additionally, the contact area 950 may have a polygonal shape, such as a rectangular shape.

As described above, the organic light emitting display device according to the first embodiment of the present invention supplies the high-level power to both sides of the high-level power line PL, thus minimizing non-uniform luminance due to the drop of a voltage caused by the resistance of the high-level power line PL. Also, since the high-level power pads HP supply the high-level power from the left and right edges of the display panel 110 and the low-level power pads LP supply the low-level power from the top and bottom edges of the display panel 110, the high-level power and the low-level power are easily supplied, and the high-level power lines PL do not overlap with any low-level power lines, thus preventing burning due to overlap between the power lines.

Figure 7:
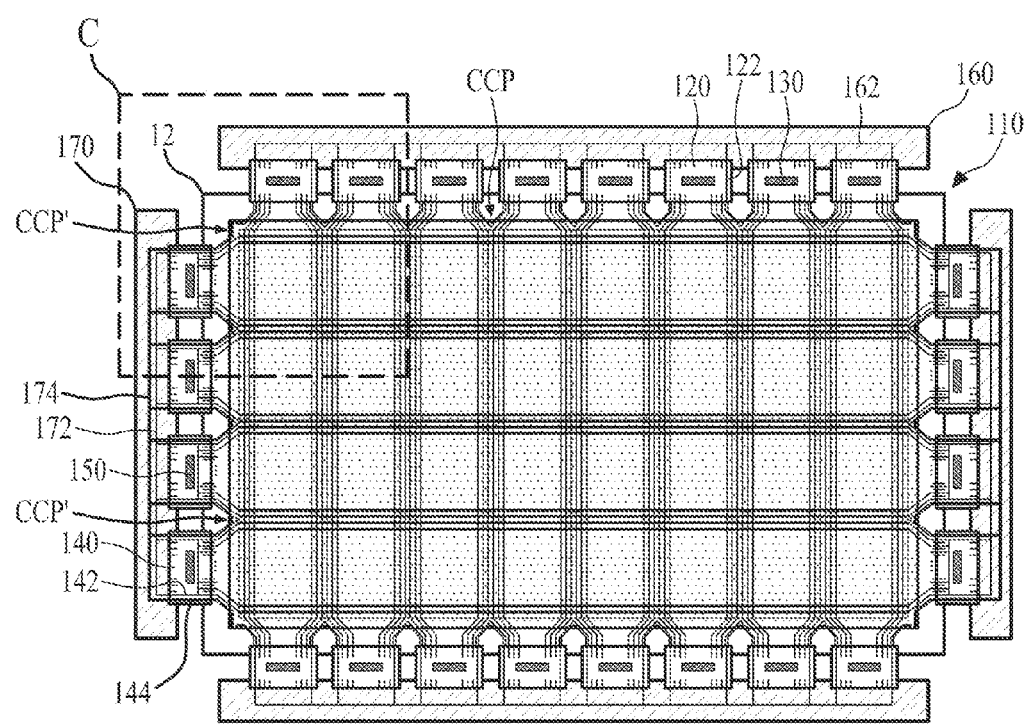
FIG. 7 is a perspective view schematically illustrating an organic light emitting display device according to a second embodiment of the present invention.
Figure 8:
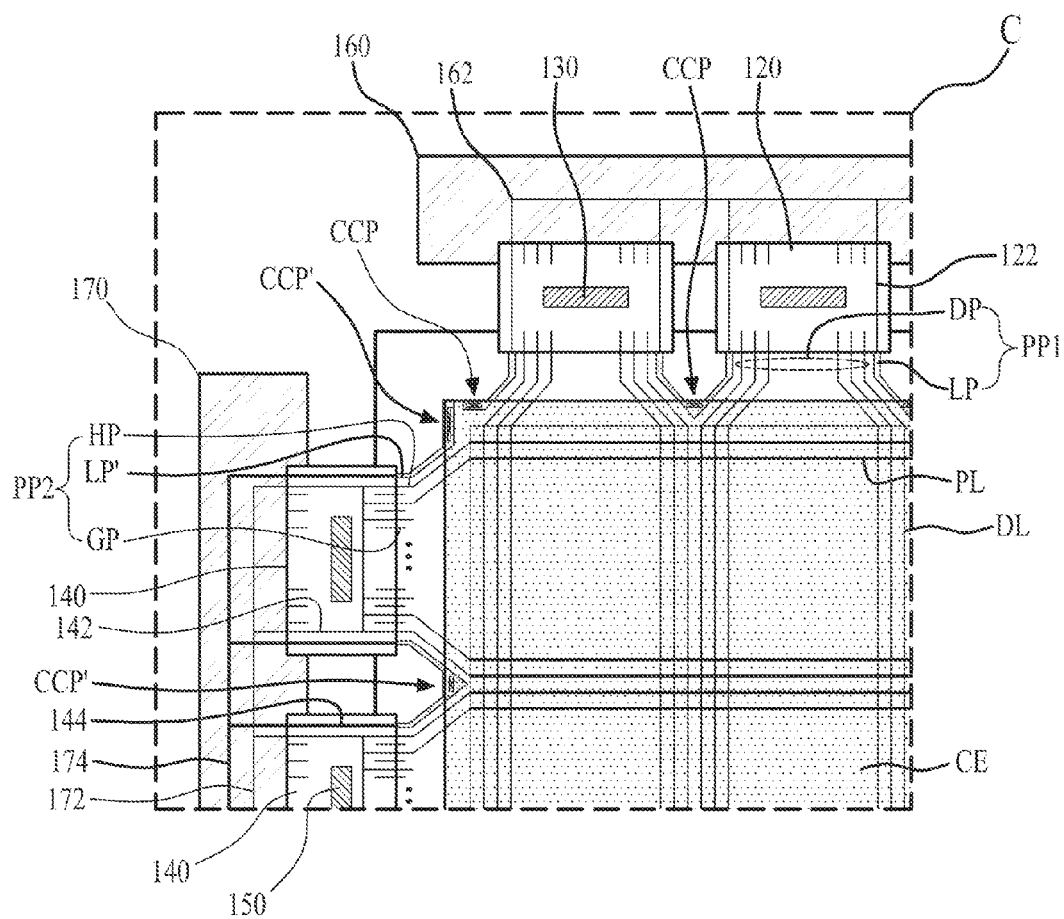
FIG. 8 is an enlarged view of a portion C of FIG. 7.

FIG. 7 is a perspective view schematically illustrating an organic light emitting display device according to a second embodiment of the present invention. FIG. 8 is an enlarged view of a portion C of FIG. 7.

Referring to FIGS. 7 and 8, the organic light emitting display device according to the second embodiment of the present invention includes a display panel 110, a plurality of first flexible circuit films 120, a plurality of data driving ICs 130, a plurality of second flexible circuit films 140, a plurality of gate driving ICs 150, a first PCB 160, and a second PCB 170. In the organic light emitting display device according to the second embodiment of the present invention having the configuration, an additional cathode connection part CCP' is additionally formed in the display panel 110, and the structure of a plurality of second pad part PP2 and the structure of the second flexible circuit film 140 have been changed according to the added additional cathode connection part CCP'. Thus, the following description will be made on only different elements.

Each of the second pad parts PP2 includes a plurality of gate pads GP respectively connected to the plurality of gate lines, a plurality of high-level power pads HP respectively connected to the high-level power lines PL, and a plurality of additional low-level power pads LP'.

Each of the gate pads GP is connected to a corresponding gate line GL through a corresponding gate link line among a plurality of gate link lines (not shown).

Each of the high-level power pads HP is formed between adjacent gate pads GP, and electrically connected to a corresponding high-level power line PL through a corresponding high-level power link line. Here, each of the high-level power lines PL is formed between adjacent gate lines to be parallel to the gate lines. Therefore, each of the high-level power pads HP supplies high-level power, supplied from a corresponding second flexible circuit film 140, to a corresponding high-level power line PL.

A plurality of additional low-level power pads LP' are formed in the third and fourth areas of the first substrate 12, and electrically connected to the respective low-level power pads LP. The cathode connection parts CCP are electrically connected to left and right edge portions of the cathode electrode layer CE to have a certain interval. Therefore, each of the additional cathode connection parts CCP' supplies the low-level power, supplied from the additional low-level power pad LP' of the second pad part PP2, to the left and right edge portions of the cathode electrode layer CE at certain intervals. In this case, a contact area between the additional cathode connection parts CCP' and the cathode electrode layer CE may be set to 10% to 90% of an overlap area between the additional cathode connection parts CCP' and the cathode electrode layer CE. That is, when the contact area between the additional cathode connection parts CCP' and the cathode electrode layer CE is less than 10% of the overlap area between the additional cathode connection parts CCP' and the cathode electrode layer CE, due to the narrow contact area between the additional cathode connection parts CCP' and the cathode electrode layer CE, a resistance of the contact increases, and thus, the heat generation of the additional cathode connection parts CCP' increases, causing the burning of the additional cathode connection parts CCP' and cathode electrode layer CE. Furthermore, when the contact area between the additional cathode connection parts CCP' and the cathode electrode layer CE exceeds 90% of the overlap area between the additional cathode connection parts CCP' and the cathode electrode layer CE, it is not easy to connect the additional cathode connection parts CCP' and the cathode electrode layer CE.

The upper additional cathode connection parts CCP' of the additional cathode connection parts CCP' are connected to a left upper corner portion and right upper corner of the cathode electrode layer CE adjacent to the uppermost cathode connection part CCP'. Also, the lower additional cathode connection parts CCP' of the additional cathode connection parts CCP' are connected to a left lower corner portion and right lower corner of the cathode electrode layer CE adjacent to the lower cathode connection parts CCP'. The remaining cathode connection parts CCP' are connected to the left and right edge portions of the cathode electrode layer CE, corresponding to respective spaces between adjacent second pad parts PP2, at certain intervals.

The additional cathode connection parts CCP' are configured identically to the cathode connection parts CCP, and thus, the descriptions of FIGS. 5 and 6 are applied to the additional cathode connection parts CCP'.

Each of the second flexible circuit films 140 supplies the high-level power to the high-level power pad HP of the second pad part PP2, and simultaneously, additionally supplies the low-level power to the additional low-level power pad LP' of the second pad part PP2. To this end, a pair of high-level power supply lines 142 electrically connected to the high-level power pad HP and a pair of low-level power supply lines 144 electrically connected to the additional low-level power pad LP' are formed in each of the second flexible circuit films 140.

The pair of high-level power supply lines 142 supply the high-level power, inputted from a high-level power input line 172 formed in the second PCB 170, to the high-level power pad HP. Furthermore, the pair of low-level power supply lines 144 supply the low-level power, inputted from a low-level power input line 174 formed in the second PCB 170, to the additional low-level power pad LP'.

The first flexible circuit films 140 supply the high-level power, supplied from the second PCBs 170, to both sides of the high-level power line PL through the second pad parts PP2, thereby minimizing the drop of the high-level power caused by the line resistance of the high-level power line PL. Furthermore, the first flexible circuit films 140 additionally supply the low-level power, supplied from the second PCBs 170, to the left and right edge portions of the cathode electrode layer CE, thereby better maintaining the constant level of the low-level power supplied to the cathode electrode layer CE. That is, the low-level power is supplied to the upper and lower edge portions of the cathode electrode layer CE at certain intervals by the second flexible circuit films 140, and simultaneously supplied to the left and right edge portions of the cathode electrode layer CE at certain intervals by the second flexible circuit films 140. Therefore, the organic light emitting display device according to the second embodiment of the present invention supplies the low-level power to the upper, lower, left, and right edge portions of the cathode electrode layer CE at certain intervals, thus better maintaining the constant level of the low-level power supplied from the cathode electrode layer CE.

The organic light emitting display device according to the second embodiment of the present invention provides the same effects as those of the organic light emitting display device according to the first embodiment of the present invention, and moreover can better maintain the constant level of the low-level power supplied to the cathode electrode layer CE.

Figure 9:
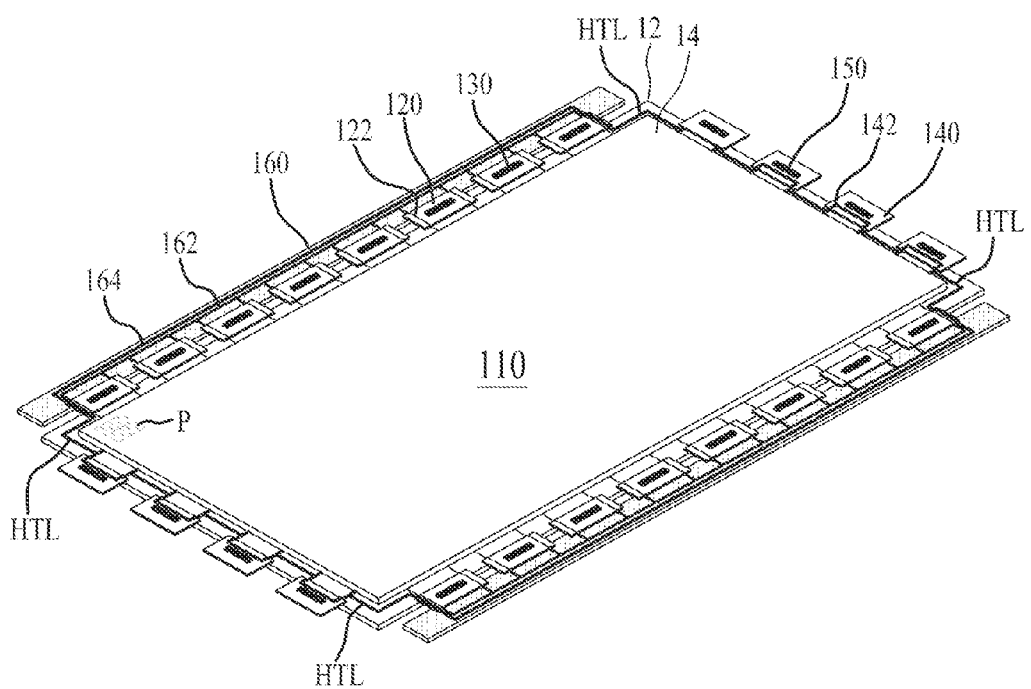
FIG. 9 is a perspective view schematically illustrating an organic light emitting display device according to a third embodiment of the present invention.
Figure 10:
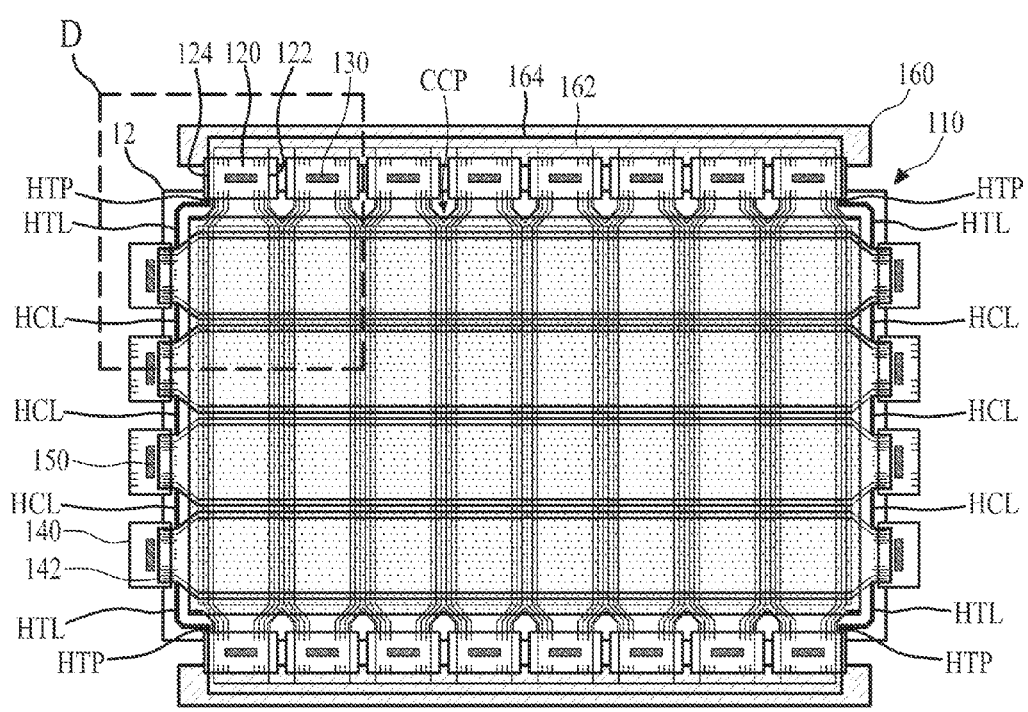
FIG. 10 is a plan view for describing a plurality of first flexible circuit films and second flexible circuit films (which are connected to a first substrate) of FIG. 9.
Figure 11:
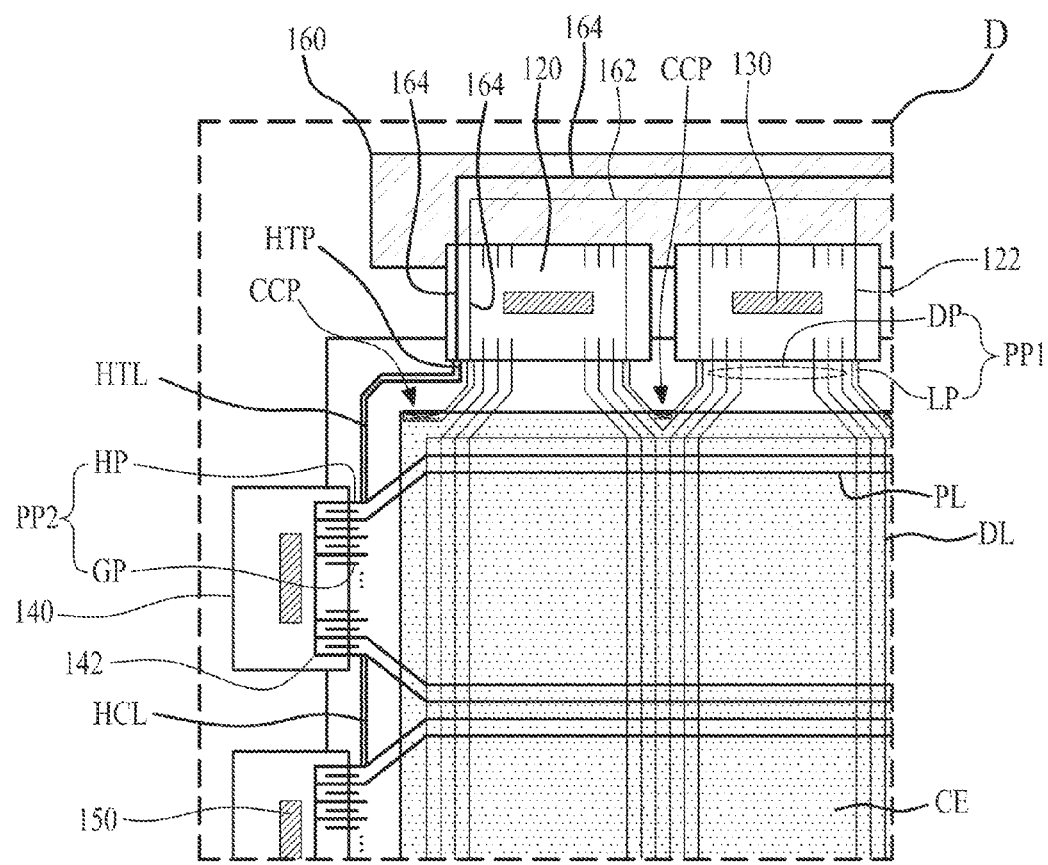
FIG. 11 is an enlarged view of a portion D of FIG. 10.

FIG. 9 is a perspective view schematically illustrating an organic light emitting display device according to a third embodiment of the present invention. FIG. 10 is a plan view for describing a plurality of first flexible circuit films and second flexible circuit films (which are connected to a first substrate) of FIG. 9. FIG. 11 is an enlarged view of a portion D of FIG. 10.

Referring to FIGS. 9 to 11, the organic light emitting display device according to the third embodiment of the present invention includes a display panel 110, a plurality of first flexible circuit films 120, a plurality of data driving ICs 130, a plurality of second flexible circuit films 140, a plurality of gate driving ICs 150, and a first PCB 160. In the organic light emitting display device according to the third embodiment of the present invention having the configuration, a high-level power transfer pad HTP and a high-level power transfer line HTL are additionally formed in the display panel 110, and the high-level power is supplied to the second flexible circuit film 140 by the added high-level power transfer pad HTP and high-level power transfer line HTL. Thus, the following description will be made on only different elements.

The display panel 110 is configured similarly to the display panel 110 of FIGS. 3 and 4, but further includes a plurality of high-level power transfer pad HTP formed in the plurality of first pad parts PP1, a high-level power transfer line HTL formed in each corner portion of the first substrate 12, and a plurality of high-level power connection lines HCL formed in respective spaces between the plurality of second pad parts PP2.

The high-level power transfer pad HTP is formed in each of the leftmost first pad parts PP1 and rightmost first pad parts PP1 of the plurality of first pad parts PP1 formed in the first and second inactive areas of the display panel 110. In this case, the leftmost first pad parts PP1 are formed in the left portion of each of the first and second inactive areas. The leftmost pad parts PP1 correspond to the leftmost data line DL. The rightmost first pad parts are formed in the right portion of each of the first and second inactive areas. The rightmost first pad parts PP1 correspond to the rightmost data line DL.

The high-level power transfer line HTL is formed in each corner portion of the first substrate 12. In this case, the high-level power transfer line HTL may be vertically bent, or may be rounded to have a certain curvature. The high-level power transfer line HTL is formed simultaneously in a process that forms the high-level power link line and the high-level power line PL. The high-level power transfer line HTL is electrically connected to the high-level power transfer pad HTP, and electrically connected to the high-level power pad HP formed in each of the upper second pad parts PP2 and lower second pad parts PP2 of the plurality of second pad parts PP2. Therefore, the high-level power supplied to the high-level power transfer pad HTP is supplied to the high-level power pad HP, formed in each of the upper and lower second pad parts PP2 of the plurality of second pad parts PP2, through the high-level power transfer line HTL. The high-level power supplied to the high-level power pad HP is supplied to the high-level power line PL through the high-level power supply line 142 formed in the second flexible circuit film 140.

The respective high-level power connection lines HCL are formed in the third and fourth inactive areas of the display panel 110 corresponding to respective spaces between the plurality of second pad parts PP2, and electrically connect the vertically adjacent high-level power pads HP of the second pad part PP2. Therefore, the high-level power (which is supplied to the high-level power pad HP of each of the upper second pad parts PP2 and the lower second pad parts PP2 through the high-level power transfer line HTL) is supplied to the high-level power pads HP of the remaining second pad parts other than the upper second pad part PP2 and the lower second pad part PP2 through the high-level power connection line HCL. That is, the high-level power connection line HCL supplies the high-level power (which is supplied to the high-level power pad HP of a previous-stage second pad part) to the high-level power pad HP of a next-stage second pad part according to a cascade structure.

Each of the first flexible circuit films 120 is configured similarly to the display panel 110 of FIGS. 3 and 4, except that leftmost first flexible circuit films 120 adhered to the leftmost first pad parts and the rightmost last flexible circuit films 120 adhered to the rightmost first pad parts further includes an additional high-level power supply line 124.

The gate driving ICs 150 respectively mounted on the second flexible circuit films 140 are the same as the first embodiment of the present invention except a scheme of supplying the gate control signal. That is, the gate driving ICs 150, respectively mounted on the uppermost second flexible circuit films 140 and the lowest second flexible circuit films 140, receive the gate control signal through the leftmost first flexible circuit films 120 and the rightmost first flexible circuit films 120, the leftmost first pad part PP1 and the rightmost first pad part PP2, a plurality of gate control signal link lines (not shown) formed in respective corner areas of the first substrate 12, and the uppermost second flexible circuit films 140 and the lowest second flexible circuit films 340, respectively. Each of the gate driving ICs 150, respectively mounted on the remaining second flexible circuit films 140 other than the uppermost second flexible circuit films 140 and the lowest second flexible circuit films 140, receives the gate control signal from a previous-stage second flexible circuit film 140 through a gate control signal transfer line (not shown) formed between adjacent second pad parts PP2.

The first PCB 160 is electrically connected to each of the first flexible circuit films 120 adhered to the respective first pad parts PP1 in the first and second inactive areas of the display panel 110. The first PCB 160 supplies the low-level power to the first flexible circuit films 120, and supplies the high-level power to the leftmost first flexible circuit film 120 and the rightmost first flexible circuit film 120. To this end, a low-level power input line 162 connected to the low-level power supply line 122 formed in the leftmost flexible circuit film 120 is formed in the first PCB 160, and moreover, a high-level power input line 166 connected to the additional high-level power supply line 124 of each of the leftmost first flexible circuit film 120 and the rightmost first flexible circuit film 120 is formed in the first PCB 160.

The organic light emitting display device according to the third embodiment of the present invention provides the same effects as those of the organic light emitting display device according to the first embodiment of the present invention, and moreover, the second PCB 170 of the organic light emitting display device according to the first embodiment of the present invention may be removed.

The second PCB 170 may also be removed from each of the organic light emitting display devices according to the second embodiment of the present invention by the same scheme as that of the organic light emitting display device according to the third embodiment of the present invention. In the organic light emitting display devices according to the second embodiment of the present invention, the uppermost and lowest additional cathode connection parts CCP' of the plurality of additional cathode connection parts CCP' may receive the low-level power through the low-level power transfer line (not shown) and the low-level power transfer pad (not shown) formed at each corner portion of the first substrate 12, and the remaining additional cathode connection parts CCP' other than the uppermost and lowest additional cathode connection parts CCP' may respectively receive the low-level power from the uppermost and lowest additional cathode connection parts CCP' through a plurality of low-level power connection lines (not shown) that are additionally formed in respective spaces between the second pad parts PP2 other than the uppermost and lowest additional cathode connections parts CCP', and the additional low-level power supply line (not shown) that is additionally formed in the second flexible circuit film 140. In the organic light emitting display devices according to the second embodiment of the present invention, the high-level power may be supplied to the high-level power pad HP of each of the second pad parts PP2 in the same scheme as that of In the organic light emitting display devices according to the third embodiment of the present invention. As a result, in the organic light emitting display devices according to the second embodiment of the present invention, when the second PCB 170 is removed from the In the organic light emitting display devices according to the second embodiment of the present invention illustrated in FIGS. 7 and 8, the first PCB 160 is connected to the first flexible circuit films 120, supplies the low-level power to the first flexible circuit films 120, and supplies both the high-level power and the low-level power to the second flexible circuit films 140 through some of the first flexible circuit films 120 and the first substrate 12.

As described above, the organic light emitting display device of the present invention supplies the high-level power to both sides of the high-level power line PL, thus minimizing non-uniform luminance due to the drop of a voltage caused by the resistance of the high-level power line PL.

Moreover, since the high-level power pad HP for supplying the high-level power to a pixel is separated from the low-level power pad for supplying the low-level power to a pixel P, the high-level power and the low-level power are easily supplied, and the high-level power line PL does not overlap the low-level power line, thus preventing burning due to overlap between the power lines.

Moreover, by supplying the low-level power to the upper, lower, left, and right edge portions of the cathode electrode layer CE, the organic light emitting display device of the present invention can better maintain the constant level of the low-level power supplied to the cathode electrode layer CE.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An organic light emitting display device comprising:
a display panel that comprises:
   a plurality of pixels;
   a cathode layer connected to the plurality of pixels to supply a first supply voltage to the pixels;
   a plurality of supply voltage pads; and
   a plurality of cathode connection parts coupled to the cathode layer to supply the first supply voltage to the cathode layer from the plurality of supply voltage pads,
wherein each of the cathode connection parts is in contact with the cathode layer through a contact area, wherein the contact area is between 10% and 90% of an overlapping area of the cathode connection part and the cathode layer;
wherein each cathode connection part comprises an electrode layer that overlaps with the cathode layer, wherein the overlapping area of the cathode connection part and the cathode layer is the overlapping area between the electrode layer and the cathode layer, and
wherein each cathode connection part comprises one or more voltage link lines connecting the electrode layer with respective ones of the supply voltage pads.

2. An organic light emitting display device comprising:
a display panel that comprises:
   a plurality of pixels;
   gate lines connected to the pixels;
   a cathode layer connected to the plurality of pixels to supply a first supply voltage to the pixels;
   a plurality of supply voltage pads; and
   a plurality of cathode connection parts coupled to the cathode layer to supply the first supply voltage to the cathode layer from the plurality of supply voltage pads,
wherein each of the cathode connection parts is in contact with the cathode layer through a contact area, wherein the contact area is between 10% and 90% of an overlapping area of the cathode connection part and the cathode layer, and
wherein each cathode connection part comprises an electrode layer that overlaps with the cathode layer, wherein the overlapping area of the cathode connection part and the cathode layer is the overlapping area between the electrode layer and the cathode layer, and wherein the electrode layer and the gate lines are formed in a same conductive layer.

3. The organic light emitting display device of claim 1, wherein, for each cathode connection part, the contact area comprises:
one or more intermediate conductive layers located between the cathode layer and the electrode layer that electrically connect the cathode layer with the electrode layer.

4. An organic light emitting display device comprising:
a display panel that comprises:
   a plurality of pixels;
   data lines connected to the pixels;
   a cathode layer connected to the plurality of pixels to supply a first supply voltage to the pixels;
   a plurality of supply voltage pads; and
   a plurality of cathode connection parts coupled to the cathode layer to supply the first supply voltage to the cathode layer from the plurality of supply voltage pads,
wherein each of the cathode connection parts is in contact with the cathode layer through a contact area, wherein the contact area is between 10% and 90% of an overlapping area of the cathode connection part and the cathode layer,
wherein each cathode connection part comprises an electrode layer that overlaps with the cathode layer, wherein the overlapping area of the cathode connection part and the cathode layer is the overlapping area between the electrode layer and the cathode layer, and
wherein, for each cathode connection part, the contact area comprises one or more intermediate conductive layers located between the cathode layer and the electrode layer that electrically connect the cathode layer with the electrode layer, and at least one of the intermediate conductive layers and the data lines are formed in a same conductive layer.

5. The organic light emitting display device of claim 3, wherein a first layer of the intermediate conductive layers is formed from Copper and a second metal layer of the intermediate conductive layers is formed from Molybdenum-Titanium.

6. The organic light emitting display device of claim 3, wherein at least one of the intermediate conductive layers and supply voltage pads are formed from a same conductive material that is transparent.

7. The organic light emitting display device of claim 3, wherein the one or more intermediate conductive layers comprise:
a first intermediate conductive layer in contact with the electrode layer;

a second intermediate conductive layer on the first intermediate conductive layer and in contact with the first intermediate conductive layer through a hole in a planarizing layer; and wherein the cathode layer is in contact with the second intermediate conductive layer through a hole in a bank layer.

8. The organic light emitting display device of claim 7, wherein the display panel further comprises gate lines and data lines connected to the pixels, and wherein:

the electrode layer and the gate lines are formed in a first conductive layer during a first process step;

the first intermediate contact layer and data lines are formed in a second conductive layer during a second process step, and the second intermediate contact layer and the supply voltage pads are formed from a same conductive material that is transparent.

9. The organic light emitting display device of claim 1, wherein the electrode layer is polygonal.

10. The organic light emitting display device of claim 9, wherein the electrode layer is triangular.

11. The organic light emitting display device of claim 1, wherein the contact area is rectangular.

* * * * *